(12) United States Patent
Mo et al.

(10) Patent No.: US 10,195,408 B2
(45) Date of Patent: Feb. 5, 2019

(54) TRANSDERMAL DRUG DELIVERY SYSTEM CONTAINING DONEPEZIL

(71) Applicant: NAL PHARMACEUTICAL GROUP LIMITED, Causeway Bay (HK)

(72) Inventors: Y. Joseph Mo, Princeton, NJ (US); Tiffany Kawai, Princeton, NJ (US)

(73) Assignee: NAL PHARMACEUTICAL GROUP LIMITED, Causeway Bay (HK)

( * ) Notice: Subject to any disclaimer, the term of this patent is extended or adjusted under 35 U.S.C. 154(b) by 0 days.

(21) Appl. No.: 14/627,899

(22) Filed: Feb. 20, 2015

(65) Prior Publication Data

US 2015/0258036 A1  Sep. 17, 2015

Related U.S. Application Data

(60) Provisional application No. 61/942,288, filed on Feb. 20, 2014.

(51) Int. Cl.
*A61M 35/00* (2006.01)
*A61K 31/445* (2006.01)
*A61K 9/70* (2006.01)

(52) U.S. Cl.
CPC .......... *A61M 35/00* (2013.01); *A61K 9/7053* (2013.01); *A61K 9/7069* (2013.01); *A61K 9/7076* (2013.01); *A61K 31/445* (2013.01)

(58) Field of Classification Search
None
See application file for complete search history.

(56) References Cited

U.S. PATENT DOCUMENTS

| | | | |
|---|---|---|---|
| 6,670,417 B2 | 12/2003 | Foreman et al. |
| 7,858,114 B2 | 12/2010 | Ito |
| 2004/0258741 A1 | 12/2004 | Terahara et al. |
| 2007/0259028 A1 | 11/2007 | Ito |
| 2008/0131490 A1 | 6/2008 | Hanatani et al. |
| 2008/0131491 A1 | 6/2008 | Hanatani et al. |
| 2008/0138388 A1 | 6/2008 | Aida et al. |
| 2009/0098191 A1 | 4/2009 | Anderson et al. |
| 2009/0175929 A1 | 7/2009 | Terahara et al. |
| 2009/0291127 A1 | 11/2009 | Wen et al. |
| 2010/0048628 A1 | 2/2010 | Nishi et al. |
| 2010/0062045 A1 | 3/2010 | Nishi et al. |
| 2010/0080842 A1 | 4/2010 | Wen et al. |
| 2011/0059141 A1 | 3/2011 | Ito |
| 2011/0066120 A1 | 3/2011 | Lee |
| 2012/0207816 A1 | 8/2012 | Kawakami et al. |
| 2013/0053358 A1* | 2/2013 | Aida ............... A61K 9/7061 514/171 |
| 2013/0337021 A1 | 12/2013 | Ito |
| 2014/0370076 A1 | 12/2014 | Choi et al. |
| 2015/0258036 A1 | 9/2015 | Choi |

FOREIGN PATENT DOCUMENTS

| | | |
|---|---|---|
| KR | 10-2005-0037405 A | 4/2005 |
| KR | 10-2009-0009951 A | 1/2009 |
| KR | 10-2009-0085090 A | 8/2009 |
| KR | 10-2009-0101667 A | 9/2009 |
| WO | WO-2009/120002 A2 | 10/2009 |
| WO | WO-2012/002640 A2 | 1/2012 |
| WO | WO 2013/150542 A2 | 10/2013 |

OTHER PUBLICATIONS

Petroleum ester, as retrieved from the internet on Jun. 16, 2016, from <https://en.wiklipedia.org/wiki/-Petroleum_resin>.*
PCT International Search Report; International Application No. PCT/US2015/016923 dated May 20, 2015.
PCT Written Opinion of the International Searching Authority; International Application No. PCT/US2015/016923 dated May 20, 2015.
Petroleum resin, Wayback Machine, Jan. 19, 2009.
Subedi, et al., "Recent Advances in Transdermal Drug Delivery", Arch Pharm Res, vol. 33, No. 3, pp. 339-351, (2010).

* cited by examiner

*Primary Examiner* — David J Blanchard
*Assistant Examiner* — Daniel F. Coughlin
(74) *Attorney, Agent, or Firm* — Lucas & Mercanti, LLP

(57) ABSTRACT

Certain embodiments of the invention relates to a transdermal drug delivery system containing donepezil or a pharmaceutically acceptable salt thereof as an active ingredient, more specifically to a transdermal drug delivery system containing a drug-containing matrix layer comprising donepezil or its pharmaceutically acceptable salt, a styrene copolymer, a hydrogenated rosin glycerol ester, and optionally a hydrocarbon resin.

7 Claims, No Drawings

TRANSDERMAL DRUG DELIVERY SYSTEM CONTAINING DONEPEZIL

CROSS-REFERENCE TO RELATED APPLICATION

This application claims the benefit of priority from U.S. Provisional Patent Application Ser. No. 61/942,288 filed Feb. 20, 2014, the contents of which are incorporated herein by reference.

FIELD OF INVENTION

Certain embodiments of the invention relate to a transdermal drug delivery system comprising donepezil or a pharmaceutically acceptable salt thereof as an active ingredient, more specifically to a transdermal drug delivery system comprising a drug-containing matrix layer comprising donepezil or its pharmaceutically acceptable salt, a styrene copolymer, a hydrogenated rosin glycerol ester, and optionally a hydrocarbon resin.

BACKGROUND

Dementia is a disease usually accompanied by several complex cognitive disorders, such as memory loss, degeneration of intelligence, personality changes, abnormal behavior, etc. This syndrome is a cerebral degenerative disease, one of the brain diseases of the central nervous system (CNS). In this syndrome, the continuous apoptosis of neural cells induces degenerative CNS diseases, which in turn results in irreversible dysfunction of the neural network and permanent damages in corresponding functions of the body. The cerebral degenerative diseases induce apoptosis of general or specific neural cells. However, since there is no regenerative potential in differentiated neural cells, the apoptosis of neural cells results in irreversible impairment of cerebral functions.

Most therapeutic agents for Alzheimer's dementia are inhibitors for acetylcholinesterase, an enzyme that degrades acetylcholine esters. Examples include, but not limited to, donepezil (Aricept™), rivastigmin (Exelon™), galantamine (Reminyl™) and others. Among the acetylcholinesterase inhibitors, donepezil was approved for patients with dementia by the United States Food and Drug Administration (FDA) in 1996, and has been used for treating mild and moderate or severe Alzheimer's dementia. Reversible inhibition by donepezil of the acetylcholine degrading enzymes (e.g., acetylcholinesterase and butyrylcholinesterase) increases the amount of acetylcholine in the Alzheimer patients' brains, thereby activating cholinergic neurons (neurons which primarily use acetylcholine as a neurotransmitter).

Commercial formulations of donepezil have been marketed as a tablet, which is orally administered to patients suffering from Alzheimer's dementia. However, it has been reported that it is impossible for these oral formulations of donepezil to avoid the hepatic first-pass effect, and furthermore these oral dosage forms are known to produce gastrointestinal side effects such as indigestion, diarrhea, GI irritation, and others. Furthermore, patients suffering from fairly advanced dementia typically have difficulty complying with an oral dosage regimen.

U.S. Patent Publication No. 2004/0258741 and Korean Patent Publication Patent No. 10-2005-0037405, hereby incorporated by reference, teach transdermal delivery systems based on a synthetic rubber polymer such as styrene-isoprene-styrene (SIS) and/or polyisobutylene (PIB). However, since this transdermal delivery system displayed a relatively low skin penetration rate of donepezil, it was manufactured so as to have a very large surface area in order to overcome this limitation. As a result of the large size of this delivery system, patients' compliance may be decreased when the transdermal delivery system is applied to patients for 1 to 2 days through single application. In addition, if the drug concentration in the matrix of the transdermal delivery system is more than 8%, a crystalline solid is formed, which may decrease the adhesive force, lead to a non-uniform skin penetration rate of the active agent, and create storage problems, resulting in difficulty maintaining the drug therein in a high concentration.

In addition, U.S. Patent Publication Nos. 2010/0080842, 2008/0138388, and 2009/0175929, hereby incorporated by reference, teach a transdermal delivery system obtained by using an acrylic pressure-sensitive adhesive having a carboxylic acid functional group or hydroxyl functional groups, as well as using a specific absorption enhancer or a specific crystalline donepezil (a Form-B crystal) or a specific crystallization-inhibiting agent (a methacrylate copolymer having a carboxyl group). However, if an acrylic adhesive is used as a matrix of the transdermal delivery system, the drug diffusion is slowed in the pressure-sensitive adhesive layer due to the interaction between donepezil and the acrylic polymer in the layer, which also reduce movement of the drug from the pressure-sensitive adhesive layer to the skin. In order to solve this problem, Korean Patent Publication No. 10-2009-0101667, hereby incorporated by reference, has disclosed a transdermal delivery system obtained by using an EVA (ethylene vinyl acetate) adhesive and a rosin ester resin as a crystallization-inhibiting agent.

In addition, International Patent Application Publication No. WO 2011/049038, hereby incorporated by reference, discloses transdermal drug delivery system obtained by dissolving the active agent, donepezil, in an adhesive containing a styrene-isoprene-styrene block copolymer, a hydrogenated rosin glycerol ester, liquid paraffin, and an absorption enhancer. However, this transdermal drug delivery system resulted in unsatisfactory side effects such as moderate to severe skin irritation. Dementia is a chronic disease requiring application of the transdermal patch for long time. Moderate to severe skin irritation would drop the patient's compliance significantly and it would be difficult to achieve any effective treatment. Furthermore, if any use of skin irritating material, such as absorption enhancer, is eliminated from the transdermal drug delivery system to minimize the skin irritation, there is another problem such as that the skin penetration will be reduced significantly.

SUMMARY OF THE INVENTION

Certain aspects of the invention provides a transdermal drug delivery system comprising a drug containing matrix layer containing donepezil or its salt as an active ingredient, wherein the matrix layer contains a styrene copolymer, a hydrogenated rosin glycerol esters and optionally a hydrocarbon resin. In one embodiment, the transdermal drug delivery system provides not only high skin penetration rate but also continuous maintenance of therapeutically effective concentration of drug in plasma for at least 24 hours. In another embodiment, the transdermal drug delivery system reduces or prevents crystallization of donepezil even after long period of storage and minimizes skin irritation.

Thus, certain aspects of the invention provides a transdermal drug delivery system containing donepezil having high skin penetration continuously more than 24 hours, excellent stability, and reduced skin irritation.

It should be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes. All numerical ranges should be understood to include each and every numerical point within the numerical range, and should be interpreted as reciting each and every numerical point individually. The endpoints of all ranges directed to the same component or property are inclusive, and intended to be independently combinable.

DETAILED DESCRIPTION OF THE INVENTION

Certain aspects of the invention provides a transdermal drug delivery system comprising a drug containing matrix layer containing donepezil or its salt as an active ingredient, wherein the matrix layer contains a styrene copolymer, a hydrogenated rosin glycerol esters and optionally a hydrocarbon resin.

In one embodiment, the transdermal drug delivery provides not only high skin penetration rate but also continuous maintenance of therapeutically effective concentration of drug in plasma for at least 24 hours.

In another embodiment, the transdermal drug delivery system reduces or prevents crystallization of donepezil even after long period of storage and minimizes skin irritation.

Thus, certain embodiments of the invention provide a transdermal drug delivery system containing donepezil having high skin penetration continuously more than 24 hours, excellent stability, and reduced skin irritation.

In accordance with an aspect of some embodiments of the invention, there is provided a transdermal drug delivery system comprising a drug-containing matrix layer containing donepezil or its salt as an active ingredient, wherein the matrix layer contains a styrene copolymer, and a hydrogenated rosin glycerol ester. The transdermal delivery system of this and other embodiments of the invention may further comprise a hydrocarbon resin. An alternative embodiment of the invention may further contains a plasticizer. A non-exhaustive list of plasticizers that can be used include: petroleum-based oils (for example, paraffinic process oil, naphthenic process oil, aromatic process oil and the like), squalane, squalene, vegetable oils (for example, olive oil, camellia oil, tall oil, peanut oil, castor oil and the like), silicone oil, dibasic acid esters (for example, dibutyl phthalate, dioctyl phthalate and the like), liquid rubber (for example, polybutene, liquid isoprene rubber and the like), a liquid fatty acid ester (isopropyl myristate, hexyl laurate, diethyl sebacate, diisopropyl sebacate and the like), diethylene glycol, polyethylene glycol, propylene glycol, dipropylene glycol and the like.

In an alternative embodiment of the invention, the transdermal drug delivery system may consist of a backing layer, the drug-containing matrix layer, and a release layer.

In the transdermal drug delivery system according to certain embodiments of the invention, donepezil or its pharmaceutically acceptable salt is present in an amount ranging from 2 to 25% by weight, preferably 5-20% by weight, and more preferably 7-15% by weight based on the total weight of the drug-containing matrix layer.

The styrene copolymer is one or more selected from among styrene-butadiene-styrene copolymer, styrene-isoprene-styrene copolymer, styrene-ethylene/butylene-styrene copolymer and styrene-ethylene/propylene-styrene copolymer. The styrene copolymer is included in an amount ranging from 10 to 85% by weight, preferred 20-70% by weight, more preferably 30-65% by weight, and most preferably 33-55% by weight based on the total weight of the drug-containing matrix layer.

The transdermal drug delivery system according to certain embodiments of the invention may further comprise hydrogenated rosin glycerol esters and/or hydrocarbon resin in an amount ranging from 5-85% by weight, preferably 10-65% by weight, and more preferably 20-50% by weight, and most preferably 30-50% by weight, based on the total weight of the drug-containing matrix layer and the weight ratio of the hydrogenated rosin glycerol esters to hydrocarbon resin is from 1:1 to 1:4.

In the transdermal drug delivery system according to another embodiment of the invention, the hydrocarbon resin is present in an amount ranging from 10 to 85% by weight, preferred 20-70% by weight, more preferably 30-65% by weight, and most preferably 33-55% by weight based on the total weight of the drug-containing matrix layer.

The transdermal drug delivery system according to certain embodiments of the invention may contain a hydrogenated rosin glycerol ester is present in an amount ranging from 2 to 40% by weight, preferred 5-50% by weight, more preferably 5-20% by weight, and most preferably 5-15% by weight based on the total weight of the drug-containing matrix layer.

In certain embodiments of the invention, the hydrocarbon resin added is contained in the styrene copolymer. The amount of the styrene copolymer containing a hydrocarbon resin may range from 10 to 85% by weight, preferably 20-85% by weight, more preferably 30-85% by weight, and most preferably 50-85% by weight based on the total weight of the drug-containing matrix layer.

The transdermal drug delivery system according to certain embodiments of the invention provides a drug containing matrix containing: a styrene copolymer; a hydrogenated rosin glycerol ester; and optionally a hydrocarbon resin. In one embodiment, the transdermal drug delivery system provides not only increased skin penetration rate for donepezil, but also maintains consistent therapeutically effective concentration of donepezil in plasma for at least 24 hours or longer. In further embodiment, the transdermal drug delivery system can inhibit crystallization of donepezil during the storage over the long period and reduce skin irritation. Therefore, the transdermal drug delivery system according to certain embodiments of the invention can improve drug compliance of patients suffering from Alzheimer's disease.

In the transdermal drug delivery system according to certain embodiments of the invention, the donepezil or its pharmaceutically acceptable salt may be used in an amount sufficient to obtain a therapeutically effective blood concentration, for example, in an amount ranging from 2 to 25% by weight, preferably from 5 to 20% by weight, more preferably 10-17% by weight, and more preferably 7-15% by weight based on the total weight of the drug-containing matrix layer. If the amount of donepezil or its pharmaceutically acceptable salt is more than 25% by weight, drug crystals may be formed in the transdermal drug delivery system, which results in reducing adhesive force or lowering absorption rate of the drug.

The transdermal drug delivery system according to certain embodiments of the invention contains styrene copolymers as a matrix forming material. The styrene copolymer assists formation of the matrix and also helps to maintain the structure of the matrix. Donepezil or its pharmaceutically acceptable salt can be dispersed through the styrene copolymer matrix evenly. The styrene copolymer is one or more selected from among styrene-butadiene-styrene copolymer, styrene-isoprene-styrene copolymer, styrene-ethylene/butylene-styrene copolymer and styrene-ethylene/propylene-styrene copolymer. In another embodiment, the styrene copolymer is one or more selected from among commercially available copolymers. The commercially available styrene copolymers include, but not limited to, Kraton™ D1161 (Kraton Performance Polymers Inc., Huston, Tex., USA), Kraton™ D1102. The amount of the styrene copolymer is enough to form the matrix, or 20-70%, preferably 20-50% or more preferably 20-40% by weight based on the total weight of the drug-containing matrix layer.

The hydrogenated rosin glycerol ester in the transdermal drug delivery system of certain embodiments of the invention functions as tackifier, not only improving the adhesiveness of the transdermal drug delivery system, but also inhibiting crystallization of donepezil within the drug-containing matrix. Without being bound to any particular theory, a hydrogenated rosin glycerol ester, such as Foral™85 (Pinova, Inc., Brunswick, Ga., USA), has optimum polarity to contribute to improve solubility of donepezil within the drug-containing matrix comprising hydrophobic styrene copolymer. However, the inventors have also found that if the hydrogenated rosin glycerol ester is used as the only tackifier, the absorption or the skin penetration of donepezil can decrease and also skin irritation would increase.

In an alternative embodiment, the inventors also found that the problem is solved by using a hydrocarbon resin in combination. In other words, when a hydrogenated rosin glycerol ester and hydrocarbon resin was added to the matrix containing styrene copolymer, the tackiness of the drug containing matrix is improved, skin penetration of donepezil from the drug containing matrix is increased, and skin irritation is reduced significantly. On the other hand, preparing the drug containing matrix using styrene copolymer and hydrocarbon resin only, without the hydrogenated rosin glycerol ester produced more crystallization of donepezil after long storage. See Table 6. On the other hand, when a hydrogenated rosin glycerol ester and hydrocarbon resin are used in combination for the styrene copolymer containing matrix, crystallization of the drug, donepezil, is effective decreased as confirmed in certain embodiments of the invention.

The hydrocarbon resin of certain embodiments of the invention includes cyclic, acyclic, or aromatic hydrocarbon resin. Hydrocarbon resin is, for example, $C_{5-9}$ saturated acyclic hydrocarbon resin, $C_{5-9}$ saturated cyclic hydrocarbon resin. In addition, saturated hydrocarbon resin is selected from commercially available resin, such as Escorez™ 5380 (ExxonMobil Chemical Company, Houston, Tex., USA), Quintone™ R100 (Zeon Chemicals L.P., Louisville, Ky., USA), or others. In one embodiment, styrene copolymer containing hydrocarbon is used for the transdermal drug delivery system is Duro-Tak™ 87-6911 (Henkel Corporation, Bridgewater, N.J., USA), and others.

In the transdermal drug delivery system of certain embodiments of the invention, the total amount of the hydrogenated rosin glycerol ester and hydrocarbon resin based on the total weight of the drug containing matrix is 10-75 wt %, preferably 40-60 wt %, or more preferably 30-50%. Furthermore, the weight ratio of the hydrogenated rosin glycerol is from 1:1 to 2:9 or 8-38 wt % based on the total weight of the matrix. When the total weight % of the hydrogenated rosin glycerol ester and the hydrocarbon resin is more than 38%, it is possible to have a side effect such as skin rash and reduced patient compliance due to the rash, or to have reduced skin penetration. On the other hand, when the total weight % of the hydrogenated rosin glycerol ester and the hydrocarbon resin is less than 8%, it is likely to have the drug crystallized out.

In one embodiment of the invention there is provided a transdermal drug delivery system comprising a drug containing matrix layer containing donepezil or its salt as an active ingredient, wherein the matrix layer contains a styrene copolymer, and optionally a hydrogenated rosin glycerol ester, provided that there is no absorption enhancer.

In another embodiment of the invention, an absorption enhancer-free transdermal drug delivery system is provided. In this alternative embodiment, a transdermal drug delivery system according to this aspect of the invention comprises a drug-containing matrix comprising donepezil or its pharmaceutically acceptable salt; a styrene copolymer; a hydrogenated rosin glycerol ester; and hydrocarbon resin but is absorption enhancer-free. The transdermal drug delivery system of certain embodiments of the invention possesses superior properties such as high skin penetration and thus, unlike conventional transdermal systems, it is possible to have a transdermal drug delivery system without an absorption enhancer. In other words, the transdermal drug delivery system of certain embodiments of the invention can avoid use of absorption enhancer such as lauryl alcohol, citric acid triethyl ester, myristic acid isopropyl ester, lactic acid cetyl ester, oleyl alcohol, sorbitan monoolate, polyethylene glycol monostearate, lauromacrogol, N-methyl-2-pyrrolidone, triacetin, pyrrothiodecane, sodium acetate, etc. Absorption enhancer-free transdermal delivery system can avoid the problems of conventional transdermal delivery system such as skin irritation, safety problem, and more.

The transdermal drug delivery system of certain embodiments of the invention may be prepared by forming the drug-containing matrix layer on a release layer and then forming a backing layer thereon. For the release layer, conventional release liners or their laminates used in the field of a transdermal drug delivery system may be used. For example, there may be used a film, a paper, or a laminates thereof, which is made of polyethylene, polyester, polyvinyl chloride, polyvinylidene chloride, etc. coated with silicone resin or fluoride resin. And also, drug non-absorbable and flexible materials conventionally used in the field of a transdermal drug delivery system may be used as the backing layer (also referred to as "backing membrane"). For example, there may be used polyolefin, polyether, a multi-layer ethylene vinyl acetate film, polyester, polyurethane, etc. The transdermal drug delivery system of certain embodiments of the invention may be prepared, for example by dissolving donepezil or its pharmaceutically acceptable salt and an acrylate-rubber hybrid adhesive, optionally along with an absorption enhancer and/or a crystallization-inhibiting agent, in an appropriate solvent (e.g., ethyl acetate, etc.), casting the resulting solution on a release liner coated with silicone followed by drying the mixture, and then laminating a backing layer.

It should be understood that the components of the transdermal drug delivery system described above may be prepared using varying combinations of the components described above, and that the particular embodiments described above are non-limiting examples of these combinations. For instance, transdermal drug delivery systems prepared according to the invention may include or exclude:

an absorption enhancer, a hydrogenated rosin glycerol ester or a plasticizer. The inclusion or absence of these components is determined on an individual basis, selected by the artisan in order to prepare a transdermal system with a desirable release profile.

The high diffusion rate provided by the transdermal drug delivery system of the present invention confers the advantage of allowing for a reduced patch size compared to less efficient transdermal patches known in the art. As a result, in certain embodiments the size of the patch according to the invention can range from about 2 $cm^2$ to about 20 $cm^2$, including e.g. 3.5, 5, 7, 10, 10.5, or 15 $cm^2$, depending on the area to be applied. In certain embodiments, smaller sizes such as 2 $cm^2$ are preferred as the small size minimizes patient discomfort and encourages compliance with the treatment regimen.

EXAMPLES

Selected embodiments of the invention will be described in further detail with reference to the following experimental and comparative examples. These examples are for illustrative purposes only and are not intended to limit the scope of the invention.

Examples 1-4

Transdermal drug delivery systems were prepared according to the components and amounts shown in Table 1. To a mixture of donepezil, a styrene copolymer, a hydrogenated rosin glycerol ester, and hydrocarbon resin, was added a mixture of cyclohexane and chloroform (1:2, v/v) as a solvent so as to attain to 30% of solid content while stirring. After stirring each mixture, the resulting each solution was casted on a release liner coated with silicone, and dried. A polyethylene film was laminated onto the resulting each layer to form a backing membrane, so as to prepare each donepezil-containing transdermal drug delivery system.

TABLE 1

| | | Example (% by weight) | | | |
|---|---|---|---|---|---|
| category | Component | 1 | 2 | 3 | 4 |
| Active ingredient | Donepezil | 10 | 10 | 10 | 10 |
| Styrene Copolymer | Kraton ™ D1161 | 37 | 37 | — | — |
| | Kraton ™ D1102 | — | — | 37 | 37 |
| Hydrogenated rosin glycerol ester | Foral ™ 85 | 16 | 12 | 16 | 12 |
| Hydrocarbon resin | Escorez ™ 5380 | 32 | 36 | 32 | 36 |
| Plasticizer | Liquid paraffin | 5 | 5 | 5 | 5 |

Examples 5-6

Transdermal drug delivery systems were prepared according to the components and amounts shown in Table 2. To a mixture of donepezil, a styrene copolymer containing a hydrocarbon resin, i.e. Duro-Tak™ 87-6911, and a hydrogenated rosin glycerol ester, was added a mixture of hexane and chloroform (1:4, v/v) as a solvent so as to attain to 50% of solid content while stirring. After stirring each mixture, the resulting each solution was casted on a release liner coated with silicone, and dried. A polyethylene film was laminated onto the resulting each layer to form a backing membrane, so as to prepare each donepezil-containing transdermal drug delivery system.

TABLE 2

| | | Example (% by weight) | |
|---|---|---|---|
| category | Component | 5 | 6 |
| Active ingredient | Donepezil | 10 | 12.5 |
| Styrene Copolymer containing a hydrocarbon resin | Duro-Tak ™ 87-6911 | 80 | 77.5 |
| Hydrogenated rosin glycerol ester | Foral ™85 | 10 | 10 |

Comparative Examples 1-8

Transdermal drug delivery systems were prepared according to the components and amounts shown in Table 3. To a mixture of donepezil, a styrene copolymer and a tackifier (a hydrogenated rosin glycerol ester, and optionally a hydrocarbon resin), was added a mixture of cyclohexane and chloroform (1:2, v/v) as a solvent so as to attain to 30% of solid content while stirring. After stirring each mixture, the resulting each solution was casted on a release liner coated with silicone, and dried. A polyethylene film was laminated onto the resulting each layer to form a backing membrane, so as to prepare each donepezil-containing transdermal drug delivery system.

TABLE 3

| | | Comparative Example (% by weight) | | | | | | | |
|---|---|---|---|---|---|---|---|---|---|
| category | Component | 1 | 2 | 3 | 4 | 5 | 6 | 7 | 8 |
| Active ingredient | Donepezil | 10 | 10 | 10 | 10 | 10 | 10 | 10 | 10 |
| Styrene Copolymer | Kraton ™ D1161 | 37 | 37 | 37 | — | — | — | 32 | 27 |
| | Kraton ™ D1102 | — | — | — | 37 | 37 | 37 | — | — |
| Hydrogenated rosin glycerol ester | Foral ™85 | 0 | 48 | 8 | — | 48 | 75 | 53 | 58 |
| Hydrocarbon resin | Escorez ™ 5380 | 48 | — | 40 | 48 | — | 40.5 | — | — |
| Plasticizer | Liquid paraffin | 5 | 5 | 5 | 5 | 5 | 5 | 5 | 5 |

Comparative Example 9

To a mixture of donepezil (10 wt %) and a styrene copolymer containing a hydrocarbon resin, i.e. Duro-Tak™ 87-6911, was added a mixture of hexane and chloroform (1:4, v/v) as a solvent so as to attain to 50% of solid content while stirring. After stirring the mixture, the resulting each solution was casted on a release liner coated with silicone, and dried. A polyethylene film was laminated onto the resulting each layer to form a backing membrane, so as to prepare each donepezil-containing transdermal drug delivery system.

Experimental Example 1. Measurement of Skin Penetration Rate

The transdermal drug delivery systems prepared in Examples 1, 3, and 4, Comparative Examples 2, 5, 7 and 8 were applied onto hairless mouse skins, for determining their skin penetration rates. Specifically, skins were excised from hairless mice (6 to 8 weeks old) right before the experiment. Each transdermal drug delivery system was cut in a size of 2 $cm^2$ and then attached to the isolated skins.

Each resulting skin was fixed in each Flow-Through Diffusion Cell with a clamp thereof. To the receiver thereof, was added an isotonic phosphate buffer solution (pH 6.0). While the diffusion cell was maintained at 37° C. with stirring by a magnetic stirrer, samples were collected at an interval of 4 hours for 24 hours. The samples were subject to quantitative analysis using high-performance liquid chromatography under the conditions in Table 4.

TABLE 4

| | |
|---|---|
| Column | C-18 (Gemini, 10 cm, 5 µm) |
| Mobile phase | Acetonitrile/phosphate buffer (pH 2.7) = 70/30 |
| Flow rate | 1 mL/min |
| Wavelength | 315 nm |
| Temperature | 30° C. |

Table 5 shows the results obtained by measuring skin penetration rates as in the above.

TABLE 5

| | Skin Penetration Rate (µg/cm$^2$/h)<br>(Average ± Standard Deviation) |
|---|---|
| Example 1 | 13.21 ± 1.01 |
| Example 3 | 16.29 ± 0.71 |
| Example 4 | 18.03 ± 2.50 |
| Comparative Example 2 | 10.36 ± 0.95 |
| Comparative Example 5 | 9.59 ± 0.50 |
| Comparative Example 7 | 9.06 ± 0.40 |
| Comparative Example 8 | 7.37 ± 0.23 |

From the results shown in Table 5, it can be seen that the transdermal drug delivery system obtained by using a hydrogenated rosin glycerol ester and hydrocarbon resin in combination certain embodiments of the invention showed remarkably increased skin penetration rate, in comparison with those obtained by using a hydrogenated rosin glycerol ester only.

Experimental Example 2. Evaluation of Crystallization

The transdermal drug delivery systems prepared in Examples 1-6 and Comparative Examples 1, 3, 4, 6 and 9 were stored at room temperature for 3 months, formation of crystals in these samples were monitored visually. The result is presented in Table 6.

TABLE 6

| | Evaluation of Crystallization in the Transdermal Drug Delivery System |
|---|---|
| Example 1 | No crystal was observed. |
| Example 2 | No crystal was observed. |
| Example 3 | No crystal was observed. |
| Example 4 | No crystal was observed. |
| Example 5 | No crystal was observed. |
| Example 6 | No crystal was observed. |
| Comparative Example 1 | Crystal was formed after one day. |
| Comparative Example 3 | Crystal was formed after two months. |
| Comparative Example 4 | Crystal was formed after one day. |
| Comparative Example 6 | Crystal was formed after two months. |
| Comparative Example 9 | Crystal was formed after one month. |

From the result in Table 6, it is confirmed that no crystals were observed in the transdermal drug delivery systems prepared by the present invention. However, in Comparative Examples 1, 3, 4, 6, and 9 whose transdermal drug delivery systems were prepared using only hydrocarbon resin as the tackifier, formation of donepezil crystal was observed in all of them.

Experimental Example 3. Evaluation of Skin Irritation

The transdermal drug delivery systems prepared in Examples 5 and 6 and Comparative Examples 2 and 5 were cut in size of 4 cm$^2$ and applied to skins of three (3) volunteers to evaluate the skin irritation properties. The result is presented in Table 7.

TABLE 7

| | Evaluation of Skin Irritation |
|---|---|
| Example 5 | No skin irritation was observed. |
| Example 6 | No skin irritation was observed. |
| Comparative Example 2 | Skin irritation was observed. |
| Comparative Example 5 | Skin irritation was observed. |

From the result in Table 7, it is confirmed that no skin irritation was observed by the transdermal drug delivery systems prepared by the present invention. However, Comparative Examples 2 and 5 both showed skin irritation.

We claim:

1. A transdermal drug delivery system comprising:
    a drug containing matrix layer consisting of:
        7-15% by weight of donepezil or a pharmaceutically acceptable salt thereof based on a total weight of the drug-containing matrix layer;
        33-55% by weight of a styrene copolymer based on a total weight of the drug-containing matrix layer; and
        8-38% by weight of a hydrocarbon resin and a hydrogenated rosin glycerol ester based on a total weight of the drug-containing matrix layer.

2. The transdermal drug delivery system of claim 1, wherein the styrene copolymer is one or more selected from the group consisting of styrene-butadiene-styrene copolymer, styrene-isoprene-styrene copolymer, styrene-ethylene/butylene-styrene copolymer and styrene-ethylene/propylene-styrene copolymer.

3. The transdermal drug delivery system of claim 1, wherein weight ratio of the hydrogenated rosin glycerol esters to hydrocarbon resin is from 1:1 to 1:4.

4. The transdermal drug delivery system of claim 1, wherein the hydrocarbon resin is selected from the group consisting of cyclic, acyclic, or aromatic hydrocarbon resin.

5. The transdermal drug delivery system of claim 1, wherein the hydrocarbon resin is selected from the group consisting of $C_{5-9}$ acyclic hydrocarbon resin, $C_{5-9}$ cyclic hydrocarbon resin.

6. A transdermal drug delivery system consisting of a backing layer, a drug-containing matrix layer, and a release layer,
    wherein the drug containing matrix layer consists of:
        7-15% by weight of donepezil or a pharmaceutically acceptable salt thereof based on a total weight of the drug-containing matrix layer;
        33-55% by weight of a styrene copolymer based on a total weight of the drug-containing matrix layer; and
        8-38% by weight of a hydrocarbon resin and a hydrogenated rosin glycerol ester based on a total weight of the drug-containing matrix layer.

7. A transdermal drug delivery system comprising:
    a drug containing matrix layer consisting of:
        donepezil or a pharmaceutically acceptable salt thereof;

a styrene copolymer;
a hydrocarbon resin;
a hydrogenated rosin glycerol ester;
and a plasticizer.

* * * * *